US00RE34618E

United States Patent [19]

Ogawa et al.

[11] E Patent Number: Re. 34,618

[45] Reissued Date of Patent: May 24, 1994

[54] INJECTION OF NICARDINPINE HYDROCHLORIDE AND PROCESS FOR THE PRODUCTION THEREOF

[75] Inventors: Katayasu Ogawa, Saitama; Go Ohtani; Shoji Yokota, both of Tokyo; Masayoshi Aruga, Saitama, all of Japan

[73] Assignee: Yamanouchi Pharmaceutical Co., Ltd., Tokyo, Japan

[21] Appl. No.: 791,358

[22] Filed: Nov. 14, 1991

Related U.S. Patent Documents

Reissue of:

[64] Patent No.: 4,880,823
Issued: Nov. 14, 1989
Appl. No.: 338,402
Filed: Apr. 12, 1989

U.S. Applications:

[63] Continuation of Ser. No. 140,901, Dec. 23, 1987, abandoned, which is a continuation of Ser. No. 925,462, Oct. 30, 1986, abandoned, which is a continuation of Ser. No. 735,558, May 15, 1985, abandoned.

[30] Foreign Application Priority Data

May 22, 1984 [JP] Japan ..... 59-102991

[51] Int. Cl.[5] ..... A61K 31/44

[52] U.S. Cl. ..... 514/356; 514/970

[58] Field of Search ..... 514/356, 970

[56] References Cited

U.S. PATENT DOCUMENTS 4,582,840 4/1986 Garthoff et al. ..... 514/356

FOREIGN PATENT DOCUMENTS 1142937 3/1983 Canada ..... 514/356

OTHER PUBLICATIONS

Odani et al, C.A. vol. 92 (1980) 92:104,384u.

*Primary Examiner*—Allen J. Robinson
*Attorney, Agent, or Firm*—Burgess, Ryan & White

[57] ABSTRACT

An injectable composition of nicardipine hydrochloride comprising an aqueous nicardipine hydrochloride solution containing 2–7 w/v % of polyhydric alcohol. This injectable composition can maintain its desired concentration and can be stably stored for a long period of time.

5 Claims, No Drawings

INJECTION OF NICARDINPINE HYDROCHLORIDE AND PROCESS FOR THE PRODUCTION THEREOF

Matter enclosed in heavy brackets [ ] appears in the original patent but forms no part of this reissue specification; matter printed in italics indicates the additions made by reissue.

This application is a continuation, of application Ser. No. 140,901, filed Dec. 23, 1987, now abandoned; which is a continuation of U.S. Pat. No. 925,462, filed Oct. 30, 1986, now abandoned, which in turn is a continuation of U.S. Pat. No. 735,558, filed May 15, 1985, now abandoned.

FIELD OF THE INVENTION

This invention relates to an injectable composition of nicardipine hydrochloride having a cerebral vascular dilating activity, a coronary dilator activity, and an anti-hypertension activity. Also, the invention relates to a process of producing the injectable composition. More particularly, the invention relates to an injectable composition containing nicardipine hydrochloride and 2 to 7 W/V% of a polyhydric and a process of producing thereof.

BACKGROUND OF THE INVENTION

Hitherto, oral administering formulations containing nicardipine hydrochloride have been developed but an injectable composition containing nicardipine hydrochloride has not yet been developed. This is because in the case of using the compound as an injectable composition, the compound shows a reduction in solubility according to the kind of isotonizing agent used and thus an injectable composition having a desired concentration cannot be obtained or the stability of an injectable composition if obtained is insufficient.

The inventors have investigated the possibility of obtaining a desired concentration of nicardipine hydrochloride and the stability of an injectable composition thereof by adding various additives for overcoming the above-described difficulties. As the result of the investigation, it has been found that when sodium chloride which is usually used as an isotonizing agent for injections is added, a desired concentration of nicardipine hydrochloride is not obtained and the injectable composition is insufficient in stability.

As the result of further investigations, it has been discovered that when nicardipine chloride is dissolved in water together with 2 to 7 W/V% of a polyhydric alcohol, a stable aqueous solution of nicardipine hydrochloride is unexpectedly obtained and based on the discovery, the invention has been attained.

SUMMARY OF THE INVENTION

Thus, according to an embodiment of this invention, there is provided an injectable composition of nicardipine hydrochloride containing 2 to 7 W/V% of a polyhydric alcohol.

According to another embodiment of this invention, there is provided a process of producing an injectable composition of nicardipine hydrochloride which comprises dissolving nicardipine hydrochloride and a polyhydric alcohol in an amount of 2 to 7 W/V% of the total amount to water and adjusting the pH of the solution to 2.5 to 5.

The effect of this invention is greatly increased when the pH of the aqueous solution of nicardipine hydrochloride is adjusted to 2.5 to 5 as described above.

DESCRIPTION OF THE PREFERRED EMBODIMENT

Accordingly, the invention will be explained in detail.

As the polyhydric alcohol for use in this invention, there are sorbitol, mannitol, xylitol, propylene glycol, glycerol, inositol, etc. They may be used individually or as a mixture of them. The amount of the polyhydric alcohol is about 2 to 7 W/V%, preferably about 5 W/V% based on the whole amount of the injectable composition. In addition, a certain polyhydric alcohol may show the insufficient isotonization by the use of about 2 W/V% and in such a case, the isotonization of the injectable composition may be controlled by using other isotonizing agent.

Also, if the pH of the injectable composition is lower than 2, the stability of nicardipine hydrochloride is reduced, while if the pH is higher than 6, the solubility of nicardipine hydrochloride is reduced.

There is no particular restriction about the concentration of nicardipine hydrochloride in this invention but is, as a matter of course, dependent upon the amount of the polyhydric alcohol and the pH thereof. By selecting a proper condition, a solubility of about 0.6 W/V% can be obtained.

The injectable composition of this invention is prepared by dissolving predetermined amounts of nicardipine hydrochloride and a polyhydric alcohol in water at 50 to 60° C., adjusting the pH to about 2.5 to 5, preferably about 3.5, and then adjusting the volume of the solution to a predetermined volume by the addition of water. The pH of the solution can be controlled by a mineral acid such as hydrochloric acid and, as the case may be, by a base such as sodium hydroxide, sodium hydrogencarbonate, etc.

The injectable composition of nicardipine hydrochloride thus obtained can maintain its desired concentration (higher than 0.1 W/V%) and can be stored for a long period of time without being accompanied by the change in quality or stability. In addition, it is preferred to use light-resistant ampoules for the injectable composition.

The test relating to the stability of nicardipine hydrochloride and the result thereof are shown below.

A. Effect of polyhydric alcohol (a) The case of storing at 60° C.

(i) Sample:

The injectable composition of Example 1: Sorbitol (5 W/V%)

The injectable composition of Example 2: Mannitol (5 W/V%)

The injectable composition of Example 3: Xylitol (5 W/V%)

The injectable composition of Example 4: Propylene glycol (5 W/V%)

Control: An aqueous solution of nicardipine hydrochloride (0.1 W/V%, pH 3.5) containing no polyhydric alcohol.

(ii) Storage condition for sample: Each sample was stored in a bath maintained at 60° C. and sampled at each definite period.

Quantitative determination: The quantitative determination was performed by a high performance chromatography (HPLC).

Condition of HPLC:

Column: Nucleosil $C_{18}$ (150×4 mm)

Column temperature: 40° C.

Eluent: Methanol-0.01M potassium hydrogenphosphate solution (18:7)

Detection: Ultraviolet absorption detector Wave length 254 n.m.

(iv) Result: The remaining percentage of nicardipine hydrochloride in each sampled solution is shown in the following table.

| Sample | Storage period (week) | | | |
|---|---|---|---|---|
| | 0 | 4 | 8 | 12 |
| Example 1 | 100 | 96.09 | 89.57 | 69.67 |
| Example 2 | 100 | 93.08 | 88.26 | 71.63 |
| Example 3 | 100 | 95.04 | 85.60 | 69.24 |
| Example 4 | 100 | 97.20 | 88.03 | 74.39 |
| Control | 100 | 93.47 | 77.94 | 49.13 |

(b) The case of storing at 100° C.

(i) Sample:

The injectable composition of Example 7: Sorbitol (2 W/V%)

The injectable composition of Example 8: Sorbitol (4 W/V%)

The injectable composition of Example 9: Mannitol (2 W/V%)

The injectable comopsition of Example 10: Mannitol (4 W/V%)

The injectable composition of Example 11: Xylitol (2 W/V%)

The injectable composition of Example 12: Xylitol (4 W/V%)

The injectable composition of Example 13: Propylene glycol (2 W/V%)

The injectable composition of Example 14: Propylene glycol (4 W/V%)

Control: Same as the case (a)

(ii) Storage condition of sample: Each sample was stored in a chamber at 100° C. and sampled at each definite period.

(iii) Quantitative determination: Same as the case (a).

(iv) Result: The remaining percentage of nicardipine hydrochloride in each sampled solution is shown in the following table.

| Sample | Storage day | | |
|---|---|---|---|
| | 1 | 3 | 7 |
| Example 7 | 93.18 | 75.77 | 47.45 |
| Example 8 | 92.98 | 79.62 | 49.66 |
| Example 9 | 90.35 | 74.35 | 47.87 |
| Example 10 | 92.43 | 78.27 | 50.03 |
| Example 11 | 91.76 | 75.60 | 48.06 |
| Example 12 | 94.26 | 78.43 | 50.28 |
| Example 13 | 97.06 | 79.87 | 44.58 |
| Example 14 | 92.39 | 78.02 | 45.77 |
| Control | 88.69 | 58.26 | 20.48 |

B. Influence of pH (i) Sample:

The injectable composition of the Comparison example: pH 2.0

The injectable composition of Example 15: pH 3.0

The injectable composition of Example 16: pH 4.0

The injectable composition of Example 17: pH 5.0

(ii) Test condition of sample:

Each sample was stored in a chamber maintained at 100° C. and sampled at each definite time.

(iii) Quantitative determination: Same as the case (a).

(iv) Result: The remaining percentage of nicardipine, hydrochloride in each sampled solution is shown in the following table.

| Sample | Storage time (hr.) | | | |
|---|---|---|---|---|
| | 0 | 2.5 | 5 | 10 |
| Comparison example (2.0) | 100 | 92.02 | 88.10 | 85.53 |
| Example 15 (3.0) | 100 | 98.87 | 98.74 | 95.14 |
| Example 16 (4.0) | 100 | 99.18 | 99.68 | 99.73 |
| Example 17 (5.0) | 100 | 98.36 | 97.23 | 95.40 |

The following examples are intended to illustrate this invention but not to limit it in any way.

EXAMPLE 1

About 2 liters of distilled water was heated to 50° to 60° C. and 2.5 g of nicardipine hydrochloride and 125 g of sorbitol were dissolved therein with stirring. After cooling the solution (pH about 4.5) thus obtained to room temperature, the pH thereof was adjusted to 3.5 using 0.1 N hydrochloric acid. Then, when the whole volume thereof was adjusted to 2.5 liters by the addition of distilled water and after filtering the solution, 5 ml each of the solution was filled in each light-resistant brown ampuol

EXAMPLE 2

By following the same procedure as Example 1 using the same amount of mannitol in place of sorbitol, an injectable composition was obtained.

EXAMPLE 3

By the following the same procedure as Example 1 using the same amount of xylitol in place of sorbitol, an injectable composition was obtained.

EXAMPLE 4

By following the same procedure as Example 1 using the same amount of propylene glycol in place of sorbitol, an injectable composition was obtained.

EXAMPLE 5

By the following the same procedure as Example 1 using the same amount of glycerol in place of sorbitol, an injectable composition was obtained.

EXAMPLE 6

By following the same procedure as Example 1 using the same amount of inositol in place of sorbitol, an injectable composition was obtained.

EXAMPLE 7

By following the same procedure as Example 1 using 50 g of sorbitol, an injectable composition was obtained.

EXAMPLE 8

By following the same procedure as Example 1 using 100 g of sorbitol, an injectable composition was obtained.

EXAMPLE 9

By following the same procedure as Example 2 using 50 g of mannitol, an injectable composition was obtained.

EXAMPLE 10

By following the same procedure as Example 2 using 100 g of mannitol, an injectable composition was obtained.

EXAMPLE 11

By following the same procedure as Example 3 using 50 g of xylitol, an injectable composition was obtained.

EXAMPLE 12

By following the same procedure as Example 3 using 100 g of xylitol, an injectable composition was obtained.

EXAMPLE 13

By following the same procedure as Example 4 using 50 g of propylene glycol, an injectable composition was obtained.

EXAMPLE 14

By following the same procedure as Example 4 using 100 g of propylene glycol, an injectable composition was obtained.

EXAMPLE 15

About 2 liters of distilled water was heated to 50° to 60° C. and 1.0 g of nicardipine hydrochloride and 125 g of sorbitol were dissolved therein with stirring. After cooling the solution (pH about 5.0) to room temperature, the pH of the solution was adjusted to 3.0 using 0.1 N hydrochloric acid. Then, the whole volume of the solution was adjusted to 2.5 liters by the addition of distilled water and after filtering the solution, 5 ml each of the solution was filled in each light-resistant brown ampuol.

EXAMPLE 16

By following the same procedure as Example 15 while adjusting the pH of the solution to 4.0, an injectable composition was obtained.

EXAMPLE 17

By following the same procedure as Example 15 while adjusting the pH of the solution to 5.0 using 0.1N sodium hydroxide in place of 0.1N hydrochloric acid, an injectable composition was obtained.

EXAMPLE 18

By following the same procedure as Example 1 using 62.5 g of sorbitol and 62.5 g of mannitol in place of 125 g of sorbitol, an injectable composition was obtained.

COMPARISON EXAMPLE

By following the same procedure as Example 15 while adjusting the pH of the solution to 2.0, an injectable composition was obtained.

What is claimed is:

1. A stable, injectable composition of nicardipine hydrochloride [in ampoule form] comprising an aqueous nicardipine hydrochloride solution containing 0.04 to 0.6 W/V% nicardipine hydrochloride and 2 to 7 W/V% of a polyhydric alcohol and wherein the pH of said solution is from 2.5 to 5, and the percentage of nicardipine hydrochloride remaining in said solution after a 12 week storage period at 60° C. is between 69.24 percent and 74.39 percent.

2. The stable injectable composition as claimed in claim 1, wherein the polyhydric alcohol is selected from the group consisting of sorbitol, mannitol, xylitol, propylene glycol, glycerol, and inositol.

[3. A process of producing a stable nicardipine hydrochloride injectable composition of claim 8, which process comprises dissolving nicardipine hydrochloride and a polyhydric alcohol in an amount of 2 to 7 W/V% of the whole amount of the injection in water and adjusting the pH of the solution to 2.5 to 5.]

[4. The process as claimed in claim 3, wherein the polyhydric alcohol is selected from the group consisting of sorbitol, mannitol, xylitol, propylene glycol, glycerol and inositol.]

5. The stable injectable composition of claim 1 wherein the aqueous nicardipine solution contains 0.1 to 0.6 W/V% nicardipine hydrochloride.

6. A process of producing a stable nicardipine hydrochloride injectable composition of claim 5, which process comprises dissolving nicardipine hydrochloride and a polyhydric alcohol in an amount of 2 to 7 W/V% of the whole amount of the injectable composition in water and adjusting the pH of the solution to 2.5 to 5.

7. The process as claimed in claim 6 wherein the polyhydric alcohol is selected from the group consisting of sorbitol, mannitol, xylitol, propylene glycol, glycerol, and inositol.

* * * * *